(12) United States Patent
Akita et al.

(10) Patent No.: US 7,198,367 B2
(45) Date of Patent: Apr. 3, 2007

(54) FUNDUS IMAGING APPARATUS AND FUNDUS IMAGING METHOD

(75) Inventors: Junichi Akita, Nukata-gun (JP); Naoyuki Kondo, Anjo (JP); Akihiro Fujishiro, Toyohashi (JP); Katsuyasu Mizuno, Gamagori (JP)

(73) Assignee: Nidek Co., Ltd., Gamagori-shi (JP)

( * ) Notice: Subject to any disclaimer, the term of this patent is extended or adjusted under 35 U.S.C. 154(b) by 0 days.

(21) Appl. No.: 11/363,998

(22) Filed: Mar. 1, 2006

(65) Prior Publication Data

US 2006/0197912 A1 Sep. 7, 2006

(30) Foreign Application Priority Data

Mar. 4, 2005 (JP) ............................. 2005-060051

(51) Int. Cl.
*A61B 3/14* (2006.01)
(52) U.S. Cl. ..................... 351/206; 351/207; 351/210; 351/213; 351/214; 351/216; 351/217
(58) Field of Classification Search ................ 351/206, 351/207, 210, 213, 214, 216, 217
See application file for complete search history.

(56) References Cited

U.S. PATENT DOCUMENTS 3,698,099 A * 10/1972 Matsura ...................... 351/205

(Continued)

FOREIGN PATENT DOCUMENTS

DE 39 26 652 A1 4/1991

(Continued)

OTHER PUBLICATIONS

Freeman et al., "Simultaneous Indocyanine Green and Fluorescein Angiography Using a Confocal Scanning Laser Ophthalmoscope," Archived Of Ophthalmology, vol. 116, Apr. 1998, pp. 455-463.

(Continued)

*Primary Examiner*—Evelyn A. Lester
(74) *Attorney, Agent, or Firm*—Oliff & Berridge, PLC

(57) ABSTRACT

A fundus imaging apparatus comprises: a beam emitter which simultaneously emits a first laser beam and a second laser beam having a different wavelength from the first beam; an irradiation optical system having a beam scanner which scans the emitted first and second beams in two dimensions on a fundus, the irradiation optical system being adapted to irradiate the emitted first and second beams onto the fundus; a first filter which intercepts the first and second beams reflected by the fundus and second fluorescence from the fundus by irradiation of the second beam and transmits first fluorescence from the fundus by irradiation of the first beam; a second filter which intercepts the first and second beams reflected by the fundus and the first fluorescence from the fundus and transmits the second fluorescence from the fundus; an imaging optical system having a photo-receiving element which receives the first fluorescence having passed through the first filter and the second fluorescence having passed through the second filter; a filter changer which continuously alternately disposes the first filter and the second filter in an optical path of the imaging optical system in sync with scanning by the beam scanner; and an image processing part which obtains a first fundus image based on a received light signal of the first fluorescence from the photo-receiving element and obtains a second fundus image based on a received light signal of the second fluorescence from the photo-receiving element.

5 Claims, 8 Drawing Sheets

U.S. PATENT DOCUMENTS

| | | | |
|---|---|---|---|
| 4,854,692 A * | 8/1989 | Kobayashi | 351/221 |
| 5,177,511 A | 1/1993 | Feuerstein et al. | |
| 5,353,073 A * | 10/1994 | Kobayashi | 351/221 |
| 5,396,302 A | 3/1995 | Triller et al. | |
| 6,309,070 B1 | 10/2001 | Svetliza et al. | |
| 6,341,865 B1 | 1/2002 | Muchlhoff et al. | |
| 2005/0231685 A1 | 10/2005 | Akita et al. | |
| 2006/0114411 A1* | 6/2006 | Wei et al. | 351/206 |
| 2006/0126017 A1* | 6/2006 | Mizuochi | 351/206 |

FOREIGN PATENT DOCUMENTS

| | | |
|---|---|---|
| EP | 0 363 931 A2 | 4/1990 |
| JP | A 3-500136 | 1/1991 |
| JP | A 3-51408 | 3/1991 |
| JP | A 4-197337 | 7/1992 |
| JP | A 9-10180 | 1/1997 |

OTHER PUBLICATIONS

Sharp et al., "The scanning laser ophthalmoscope—a review of it role in bioscience and medicine," Physics in Medicine and Biology, vol. 49, Apr. 2004, pp. 1085-1096.

\* cited by examiner

FUNDUS IMAGING APPARATUS AND FUNDUS IMAGING METHOD

BACKGROUND OF THE INVENTION

1. Field of the Invention

The present invention relates to a fundus imaging apparatus and a fundus imaging method.

2. Description of Related Art

Known is an apparatus which selectively performs fluorescent fundus angiography (hereinafter, FAG), i.e., visible-fluorescein fundus imaging, and indocyanin green fundus angiography (hereinafter, ICG), i.e., infrared-fluorescein fundus imaging (refer to Jpn. unexamined patent publication No. 9(1997)-10180). However, such conventional apparatus, which is arranged to separately perform the FAG (visible-fluorescein fundus imaging) and the ICG (infrared-fluorescein fundus imaging), needs much time to perform both imaging operations.

SUMMARY OF THE INVENTION

The present invention has been made in view of the above circumstances and has an object to provide a fundus imaging apparatus and a fundus imaging method capable of efficiently performing both visible-fluorescein fundus imaging and infrared-fluorescein fundus imaging.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a fundus imaging apparatus comprising: a beam emitter which simultaneously emits a first laser beam and a second laser beam having a different wavelength from the first beam; an irradiation optical system having a beam scanner which scans the emitted first and second beams in two dimensions on a fundus, the irradiation optical system being adapted to irradiate the emitted first and second beams onto the fundus; a first filter which intercepts the first and second beams reflected by the fundus and second fluorescence from the fundus by irradiation of the second beam and transmits first fluorescence from the fundus by irradiation of the first beam; a second filter which intercepts the first and second beams reflected by the fundus and the first fluorescence from the fundus and transmits the second fluorescence from the fundus; an imaging optical system having a photo-receiving element which receives the first fluorescence having passed through the first filter and the second fluorescence having passed through the second filter; a filter changer which continuously alternately disposes the first filter and the second filter in an optical path of the imaging optical system in sync with scanning by the beam scanner; and an image processing part which obtains a first fundus image based on a received light signal of the first fluorescence from the photo-receiving element and obtains a second fundus image based on a received light signal of the second fluorescence from the photo-receiving element.

According to another aspect, the present invention provides a fundus imaging method comprising the steps of: simultaneously emitting a first laser beam and a second laser beam having a wavelength different from the first beam and scanning the emitted first and second beams in two dimensions on a fundus; continuously and alternately receiving first fluorescence from the fundus resulting from the first beam and second fluorescence from the fundus resulting from the second beam in sync with scanning of the first and second beams; and obtaining a first fundus image based on a received light signal of the first fluorescence and a second fundus image based on a received light signal of the second fluorescence in alternate manner every one frame.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
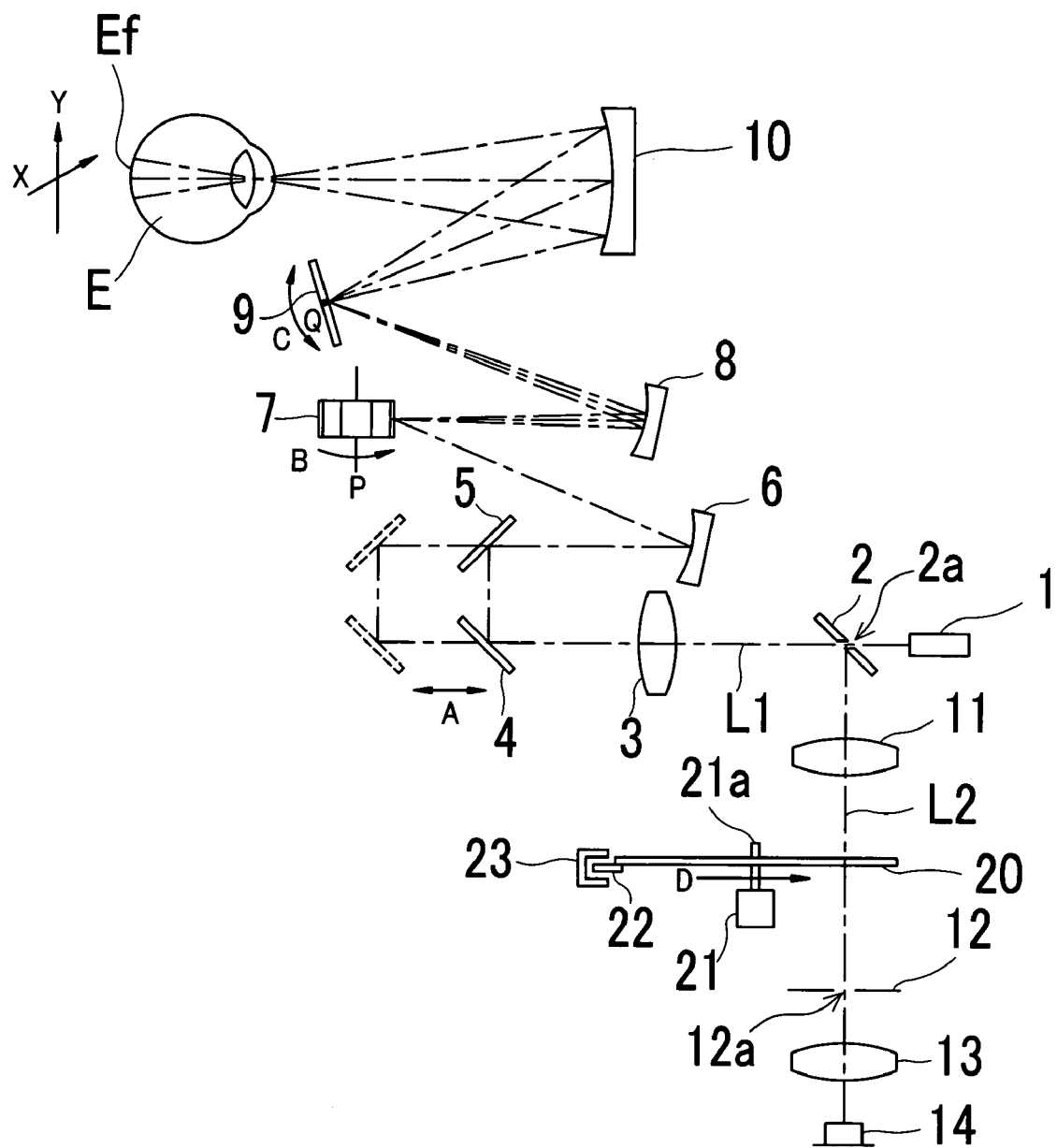
FIG. 1 is a schematic configuration view of an optical system of a fundus imaging apparatus in a preferred embodiment of the present invention.

A detailed description of a preferred embodiment of the present invention will now be given referring to the accompanying drawings. FIG. 1 is a schematic configuration view of an optical system of a fundus imaging apparatus in the present embodiment.

Figure 2:
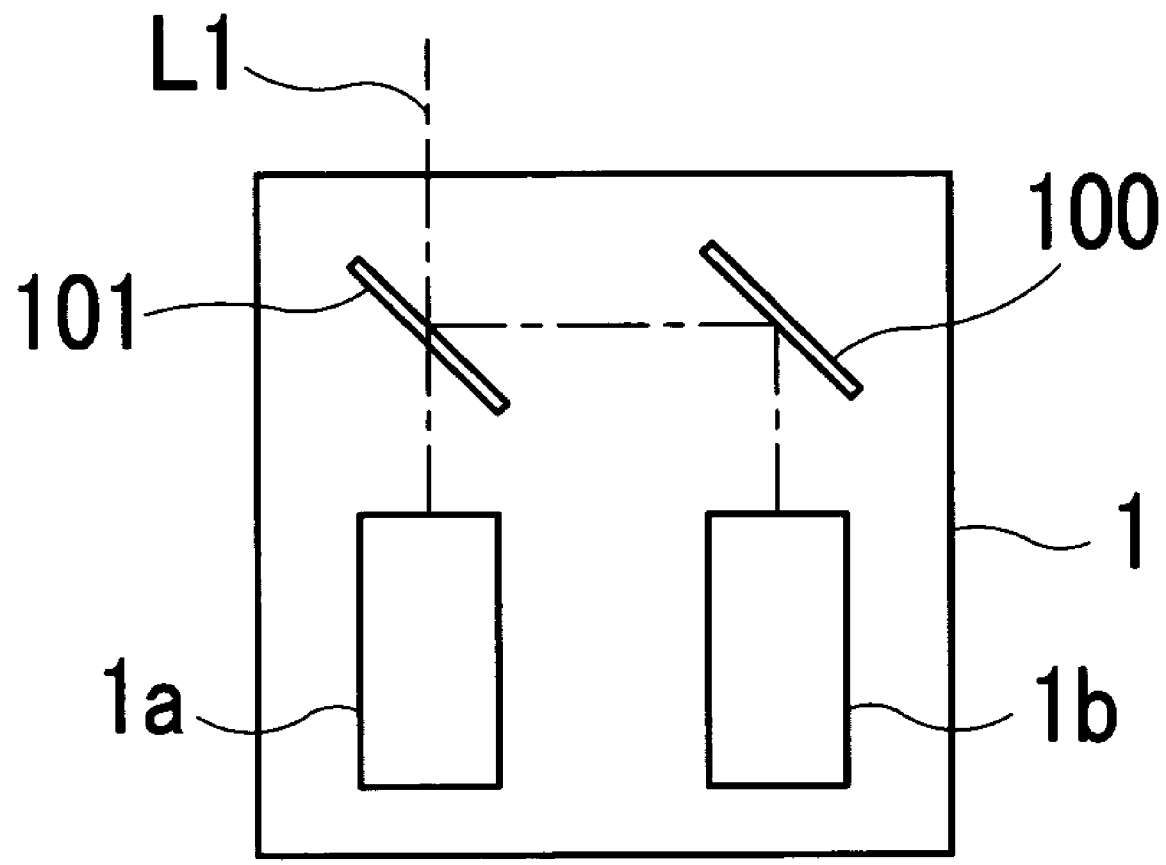
FIG. 2 is a schematic configuration view of a beam emitting part.

A beam emitting part (beam emitter) 1 includes a first laser source 1a which emits a first laser beam of wavelengths in an infrared region, a second laser source 1b which emits a second laser beam of wavelengths in a visible region, a total reflection plane mirror 100, and a dichroic mirror 101 which transmits infrared light and reflects visible light, as shown in FIG. 2. In the present embodiment, the first laser source 1a emits the first beam having a wavelength of about 780 nm. The second laser source 1b emits the second beam having a wavelength of about 480 nm. The first beam emitted from the first laser source 1a passes through the dichroic mirror 101 to travel along an optical axis L1. The second beam emitted from the second laser source 1b is reflected by the mirror 100 and the dichroic mirror 101 and thereby made coaxial with the first beam to travel along the optical axis L1.

The first beam and the second beam emitted from the beam emitting part 1 pass through an opening 2a of a perforated mirror 2 (through a substantial center of which the optical axis L1 passes) and a lens 3, and are reflected by total reflection plane mirrors 4 and 5 and a total reflection concave mirror 6 in turn, and then fall on a polygon mirror 7. The first and second beams reflected by the polygon mirror 7 are reflected by a total reflection concave mirror 8 and fall on a galvano mirror 9. The first and second beams reflected by the galvano mirror 9 are reflected by a total reflection concave mirror 10 and focused on a fundus Ef of a patient's eye E. The above optical members constitute an irradiation optical system for the first and second beams.

The mirrors 4 and 5 are arranged to be movable in a direction indicated by an arrow A in order to change the length of optical path for focus adjustment (diopter movement). The polygon mirror 7 is rotated about an axis P in a direction indicated by an arrow B in order to scan the first and second beams on the fundus Ef in a direction indicated by an arrow X. The galvano mirror 9 is swung (rotated) about an axis Q in a direction indicated by an arrow C in order to scan the first and second beams on the fundus Ef in a direction indicated by an arrow Y perpendicular to the X direction. With the above beam scanners, the first and second beams are scanned on the fundus Ef in two dimensions.

The first and second beams scanned on the fundus Ef and reflected therefrom reversely travel along the above mentioned irradiation optical system and are reflected by a surface surrounding the opening 2a of the perforated mirror 2 to travel along the optical axis L2. The opening 2a of the perforated mirror 2 is substantially conjugated with a pupil of the eye E through the lens 3. The first and second beams reflected by the perforated mirror 2 pass through a lens 11 and a filter disc 20 to come into focus on a pinhole 12a of a pinhole plate 12 (through a substantial center of which the optical axis L2 passes). The pinhole 12a is substantially conjugated with the fundus Ef through the lens 11. The first and second beams focused on the pinhole 12a pass through a lens 13 to fall on a photo-receiving element 14 having sensitivity to light of wavelengths in a visible region and an infrared region. The above optical members constitute an imaging optical system.

The diameter of the pinhole 12a in the present embodiment is fixed. Alternatively, the pinhole 12a may be formed with a variable diameter to allow changes in contrast and luminance of an image of the fundus Ef to be obtained. The photo-receiving element 14 in the present embodiment is APD (avalanche photodiode), but it is not limited thereto.

The filter disc 20 is disposed in a plane perpendicular to or inclined at a predetermined angle with respect to the optical axis L2 so that a part of the filter disc 20 is intersected by the optical axis L2. The filter disc 20 may be placed anywhere in an optical path of the imaging optical system (between the perforated mirror 2 and the photo-receiving element 14) which does not overlap with the optical path of the irradiation optical system.

The filter disc 20 is rotated about a shaft 21a in a direction indicated by an arrow D by a rotator 21 such as a motor. The rotator 21 in the present embodiment is a pulse motor, but it is not limited thereto. A sensor 23 for positional detection (rotation angle detection) of the filter disc 20 detects a reference position of the filter disc 20 when the sensor 23 is shielded by a shielding plate 22 provided in a predetermined position of the filter disc 20. The rotation angle of the filter disc 20 is adjusted based on the reference position.

Figure 3:
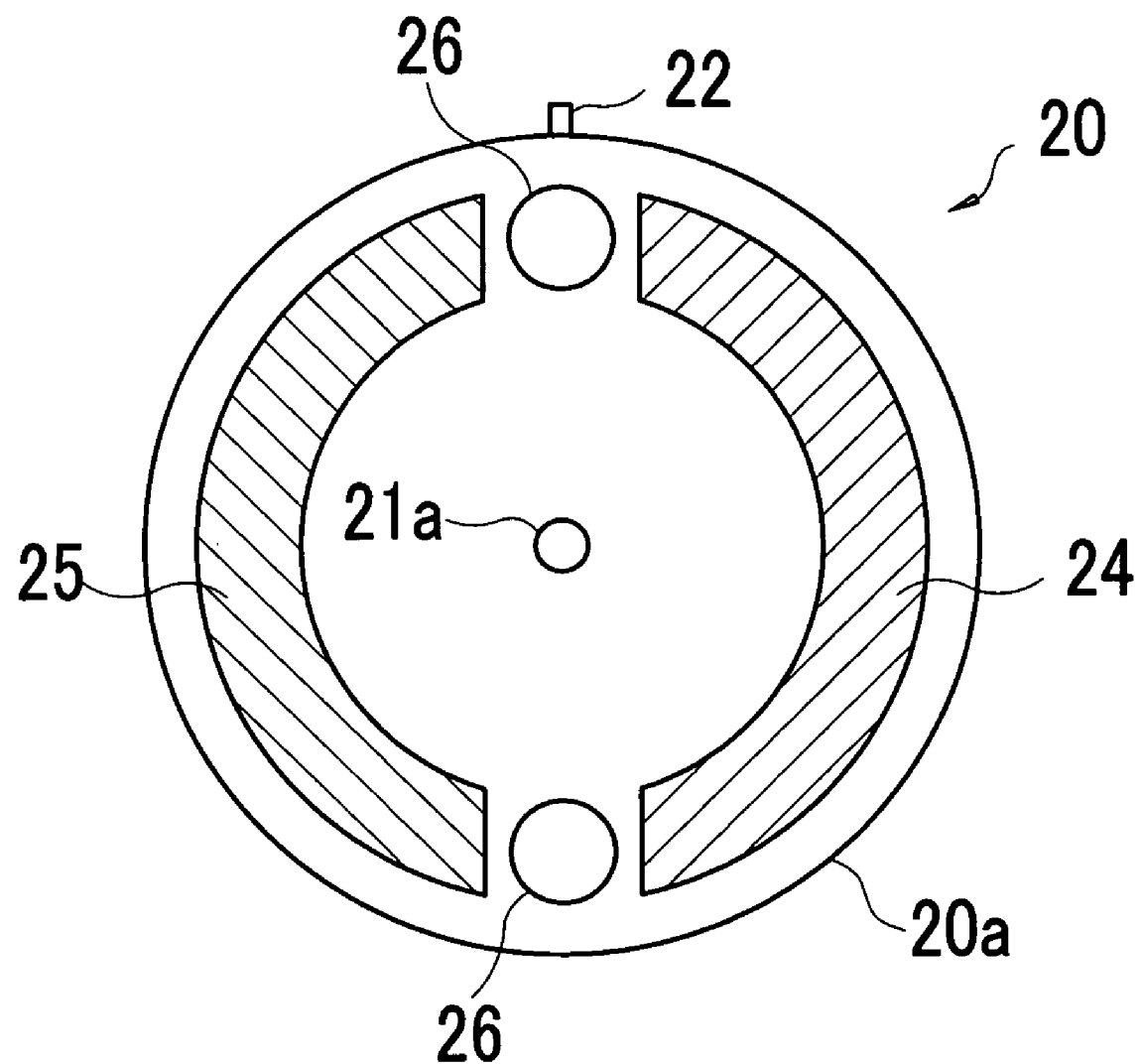
FIG. 3 is a schematic configuration view of a filter disc.

FIG. 3 is a schematic configuration view of the filter disc 20.

Figure 4A:
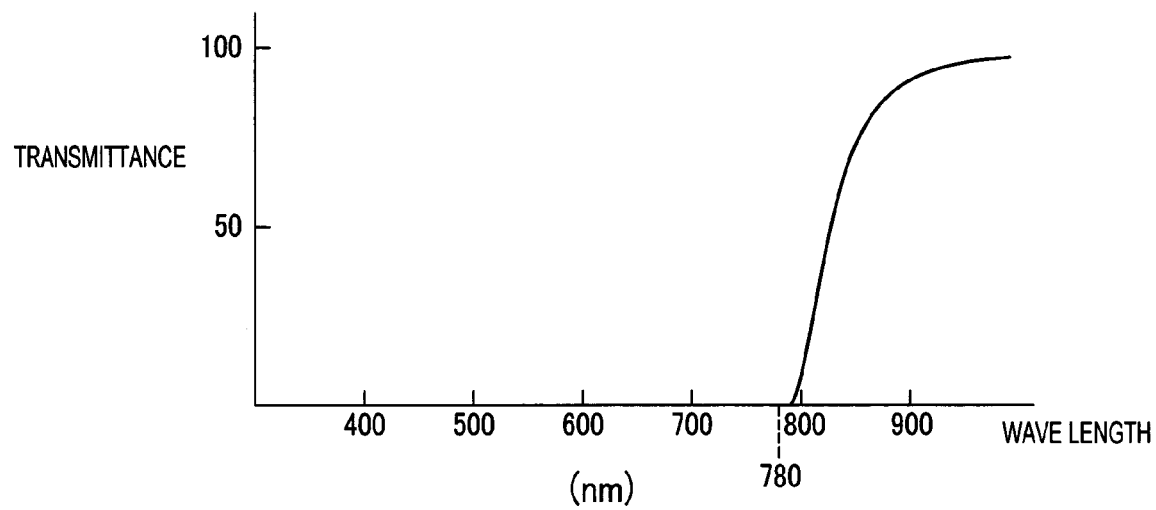
FIG. 4A is a view showing a spectral transmission property of a first filter used for infrared-fluorescein fundus imaging.
Figure 4B:
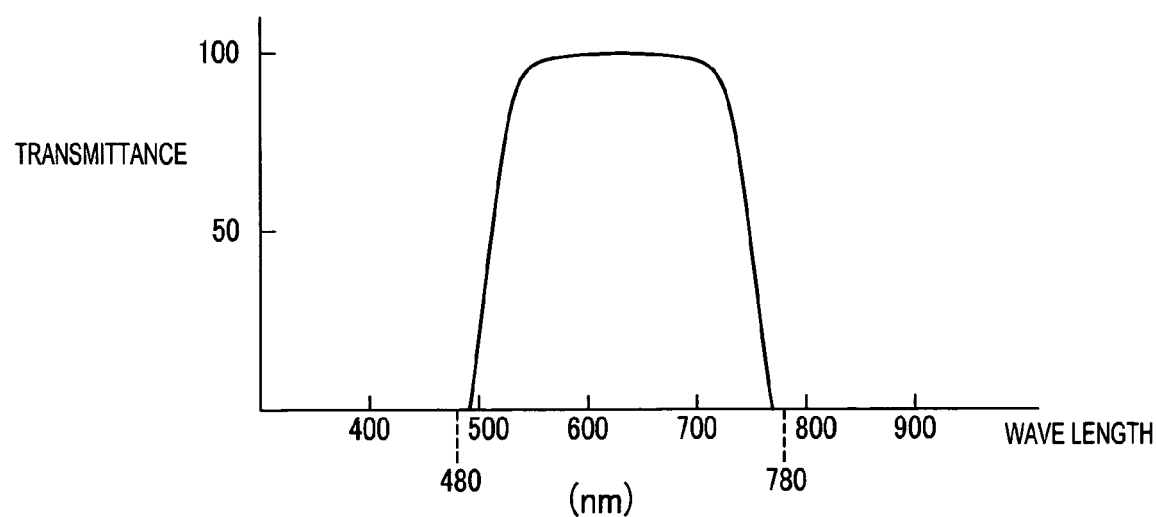
FIG. 4B is a view showing a spectral transmission property of a second filter used for visible-fluorescein fundus imaging.

On a rotary disc 20a of the filter disc 20, a first filter 24 and a second filter 25 are attached in place. The first filter 24 has a spectral transmission property as shown in FIG. 4A for infrared-fluorescein fundus imaging such as ICG. The second filter 25 has a spectral transmission property as shown in FIG. 4B for visible-fluorescein fundus imaging such as FAG. As shown in FIG. 3, each of the first and second filters 24 and 25 is of a substantial sector shape having two arcuate outer lines and two straight outer lines. These filters 24 and 25 are arranged symmetrically with respect to the center of the rotary disc 20a so that the first and second filters 24 and 25 are selectively intersected by (disposed on) the optical path of the imaging optical system that does not overlap with the optical path of the illumination optical system, that is, the optical axis L2. Those rotary disc 20a, the rotator 21, and the shaft 21a constitute a filter changer which continuously selectively disposes the first filter 24 and the second filter 25 in the optical path of the imaging optical system.

The first filter 24 intercepts the first and second beams reflected by the fundus Ef and second fluorescence produced in the fundus Ef when the second beam is irradiated as excitation light. The first filter 24 transmits first fluorescence produced in the fundus Ef when the first beam is irradiated as excitation light. On the other hand, the second filter 25 intercepts the first and second beams reflected by the fundus Ef and the first fluorescence from the fundus Ef and transmits the second fluorescence from the fundus Ef.

The rotary disc 20a of the filter disc 20 is provided with openings 26 (two openings in the present embodiment) between the first and second filters 24 and 25 as shown in FIG. 3. During alignment of the apparatus with the eye E and during normal fundus imaging, for example, either of the openings 26 is disposed in the optical path (the optical axis L2) of the imaging optical system to allow all light beams from the fundus Ef to pass therethrough to reach the photo-receiving element 14. The first filter 24, the second filter 25, and the openings 26 are arranged in a predetermined positional relationship relative to the reference position of the filter disc 20.

Figure 5:
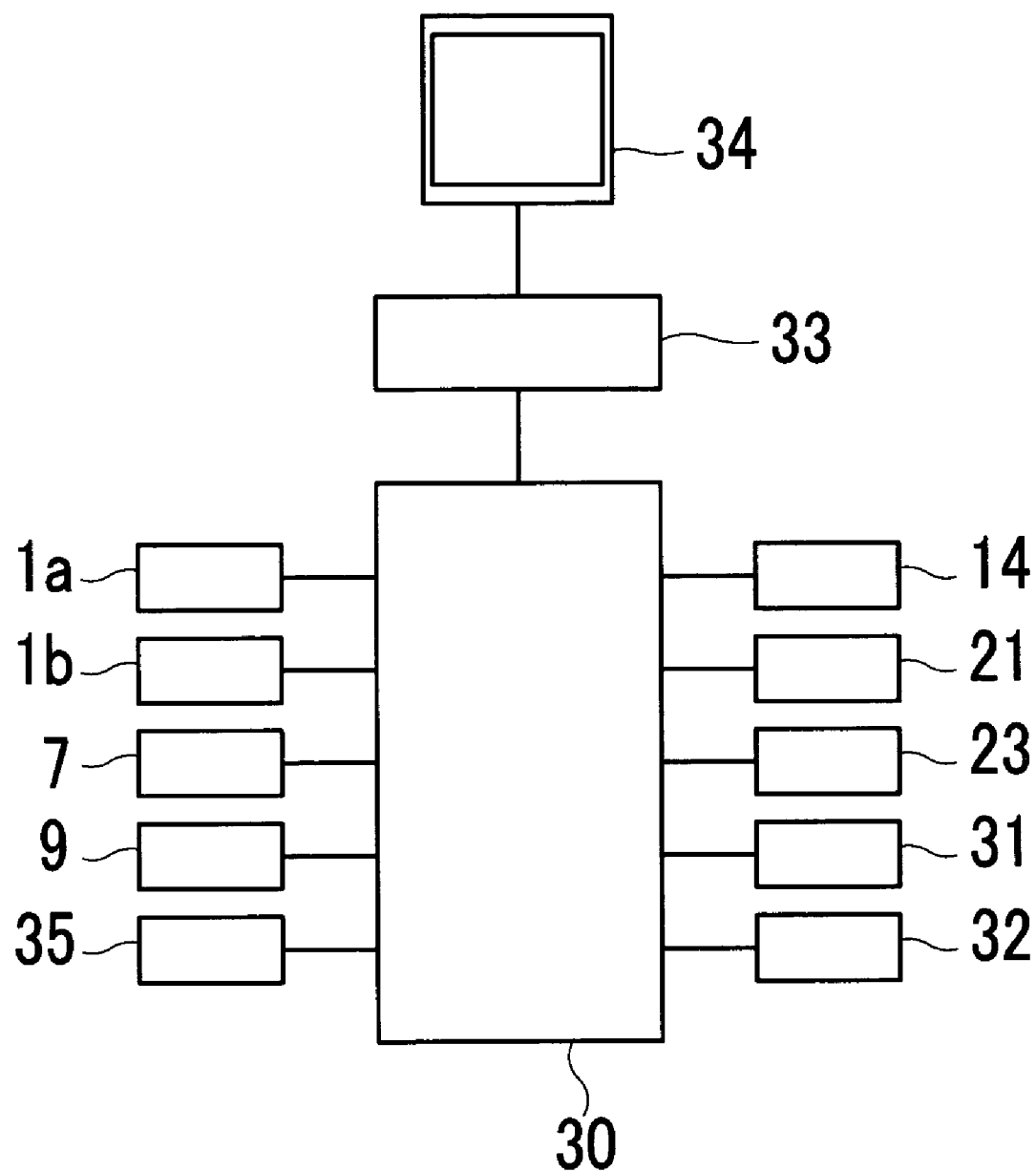
FIG. 5 is a schematic block view of a control system of the fundus imaging apparatus.

FIG. 5 is a schematic block view of a control system of the apparatus.

Connected to an arithmetic control section 30 which controls all systems of the apparatus are the first laser source 1a, the second laser source 1b, the polygon mirror 7, the galvano mirror 9, the photo-receiving element 14, the sensor 23, a moving part 31 for moving the mirrors 4 and 5, a control part 32, an image processing part 33 which obtains (generates) an image of the fundus Ef based on a received light signal of the photo-receiving element 14, a storage part 35, and others. The fundus image obtained in the image processing part 33 is displayed on a monitor 34. The control part 32 is provided thereon with various switches for operations of the apparatus such as an input part for inputting refractive power of the eye E for diopter movement, an imaging start switch, and a change switch with which the first filter 24, the second filter 25, and the openings 26 are selectively disposed in the optical axis L2.

Operations of the apparatus having the above structure will be described below. Here, a method of simultaneously performing the ICG and the FAG is explained.

Upon power-on of the apparatus, the arithmetic control part 30 drives the rotator 21 by default to rotate the filter disc 20 to dispose the opening 26 in the optical axis L2. Further, the first laser source 1a is caused to emit the infrared, first beam as illumination light for observation. When the refractive power data of the eye E previously measured by an eye refractive power measurement apparatus or the like is input to the control part 32, the arithmetic control part 30 stores the input refractive power data in the storage part 35 while driving the moving part 31 to move the mirrors 4 and 5, performing the diopter movement.

The first beam from the first laser source 1a is scanned in two dimensions on the fundus Ef by the polygon mirror 7 and the galvano mirror 9. The first beam reflected by the fundus Ef is reflected by the perforated mirror 2, passes through the opening 26, comes into focus on the pinhole 12a, and is received by the photo-receiving element 14.

The image processing part 33 generates the image of the fundus Ef based on the received light signal of the photo-receiving element 14 relating the first beam reflected from an area of the fundus Ef scanned by the polygon mirror 7 and the galvano mirror 9. The fundus image is then displayed on the monitor 34. Specifically, images corresponding to one horizontal row are obtained by rotation of one reflection surface of the polygon mirror 7. After each time the images corresponding to the one horizontal row are obtained, the galvano mirror 9 is swung (tilted) downwards stepwise, obtaining images corresponding to one frame. When the images corresponding to one frame are obtained, the galvano mirror 9 is returned to an initial upwardly tilted state corresponding to the start of scan, and then the same operation as above is repeated to obtain the images corresponding to another frame. In the present embodiment, the infrared, first beam is used as the illumination light for observation. The visible, second beam may be used instead of the first beam.

Upon pressure of the imaging switch, the arithmetic control part 30 causes the first laser source 1a to emit the infrared, first beam and the second laser source 1b to emit the visible, second beam. Further, the arithmetic control part 30 synchronously drives the polygon mirror 7, the galvano mirror 9, and the filter disc 20 respectively to obtain a desired fluorescent fundus image.

Figure 6:
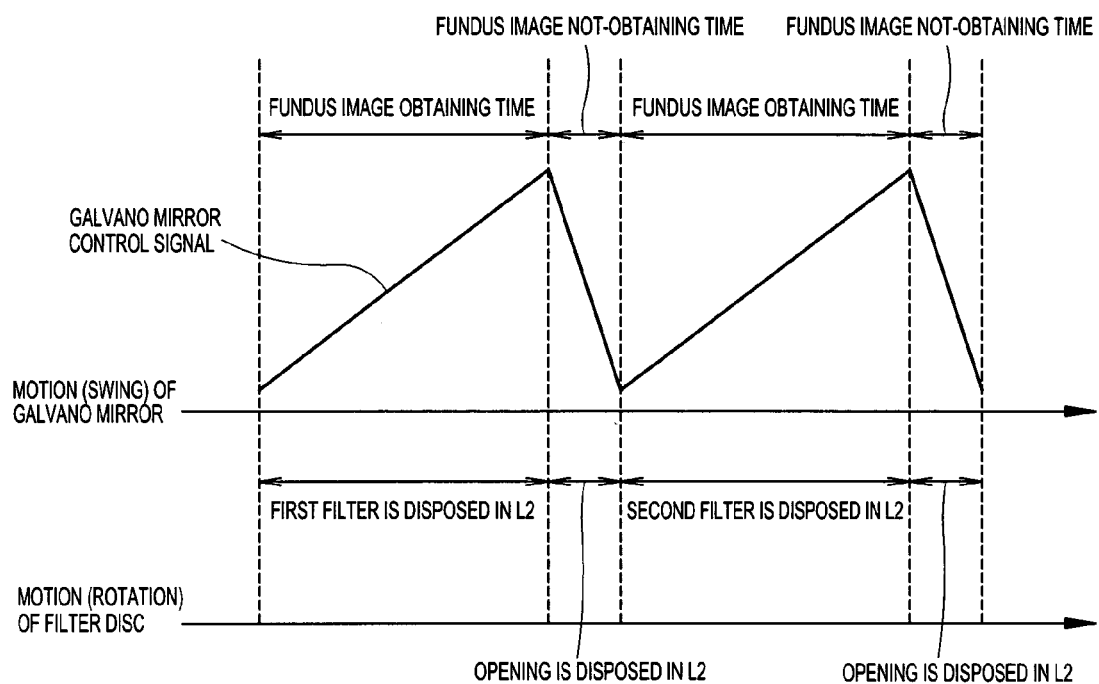
FIG. 6 is a schematic diagram showing a driving relation between a galvano-mirror and the filter disc.

The ICG and FAG are performed at a previously set frame rate and resolution. The frame rate and resolution may be fixed or be set changeably with a setting switch not shown on the control part 32. The arithmetic control part 30 rotates the polygon mirror 7 at a rotation speed appropriate to provide the set frame rate and resolution. According to this rotation speed of the polygon mirror 7, the galvano mirror 9 is swung to provide the set frame rate and resolution. By the one-way rotation of the polygon mirror 7 and the one-way swinging (downward swinging in the present embodiment) of the galvano mirror 9, as mentioned above, the fluorescent fundus images corresponding to one frame to be displayed on the monitor 34 are obtained. The arithmetic control part 30 rotates the filter disc 20 as shown in FIG. 6 so that either one of the first filter 24 and the second filter 25 is disposed in the optical axis L2 during one-way singing of the galvano mirror 9 to obtain the fluorescent fundus image, and an intermediate portion (either of the openings 26) between the first filter 24 and the second filter 25 is disposed in the optical axis L2 for a period from the termination of one scan until the galvano mirror 9 is returned to the initial tilted state corresponding to the scan start, i.e., during upward swinging of the galvano mirror 9.

The rotation angle of the filter disc 20 can be detected based on a detection signal of the sensor 23 and a pulse signal of the rotator 21, i.e., a pulse motor. The arithmetic control part 30 controls the rotation of the filter disc 20 so as to maintain the above mentioned relationship with respect to driving of the polygon mirror 7 and the galvano mirror 9. In this way, the optical path of the imaging optical system is allowed to pass through the intermediate portion (the opening 26) between the first filter 24 and the second filter 25 in response to motion (return) of the galvano mirror 9 during which no fluorescent fundus image is obtained. Thus, the fluorescent fundus image can more efficiently be obtained.

When a fluorescent agent for the ICG and a fluorescent agent for the FAG are circulated in the fundus Ef, the fluorescent fundus image by the infrared, first beam and the fluorescent fundus image by the visible, second beam are obtained. Specifically, when the first filter 24 is disposed in the optical axis L2 by rotation of the filter disc 20, only the first fluorescence from the fundus Ef, resulting from the first beam, reaches the photo-receiving element 14. When the second filter 25 is disposed in the optical axis L2, only the second fluorescence from the fundus Ef, resulting from the second beam, reaches the photo-receiving element 14. Consequently, each fluorescent fundus image can be obtained successively in timesharing manner.

The image processing part 33 obtains a fundus image based on the received light signal transmitted from the photo-receiving element 14 via the arithmetic control part 30 when the first filter 24 is disposed in the optical axis L2, and then displays the image as a fundus image by the ICG on the monitor 34. Further, the image processing part 33 obtains a fundus image based on the received light signal transmitted from the photo-receiving element 14 via the arithmetic control part 30 when the second filter 25 is disposed in the optical axis L2, and then displays the image as a fundus image by the FAG on the monitor 34. In the present embodiment, the ICG fundus image and the FAG fundus image are displayed side by side on the monitor 34. Preferably, information for distinguishing them is also displayed. As an alternative, only one of the fundus images may be selectively displayed on the monitor 34 with a switch not shown on the control part 32.

During rotation of the filter disc 20, the first filter 24 and the second filter 25 are continuously alternately disposed in the optical axis L2. Consequently, the ICG fundus image and the FAG fundus image can be obtained at substantially the same time (alternately every one frame). The variations thereof with time can be displayed as moving images on the monitor 34.

The apparatus, which is arranged to use the visible, second beam as illumination light (excitation light) for visible-fluorescence fundus imaging and scan the second beam in two dimensions as described above, allows the visible-fluorescence fundus imaging without causing glare to an examinee.

Since the infrared, first beam and the visible, second beam are emitted simultaneously, respective fluorescent fundus images can be obtained at the same time, thus reducing a time needed for inspection (medical examination). Further, a single photo-receiving element receives the first fluorescence resulting from the infrared, first beam from the fundus Ef and the second fluorescence resulting from the visible, second beam. This makes it possible to reduce the number of optical components, substrate parts, and others. Accordingly, a downsized apparatus can be realized.

Although the apparatus in the above embodiment is arranged to perform one manner of infrared-fluorescence fundus imaging and one manner of visible-fluorescence fundus imaging, it may be arranged to perform a plurality of manners of fluorescence fundus imaging. In such cases, the type and the number of filters provided in the filter disc 20 may be determined according to the types and the number, or the like, of the laser sources provided in the laser emitting part 1.

Figure 7:
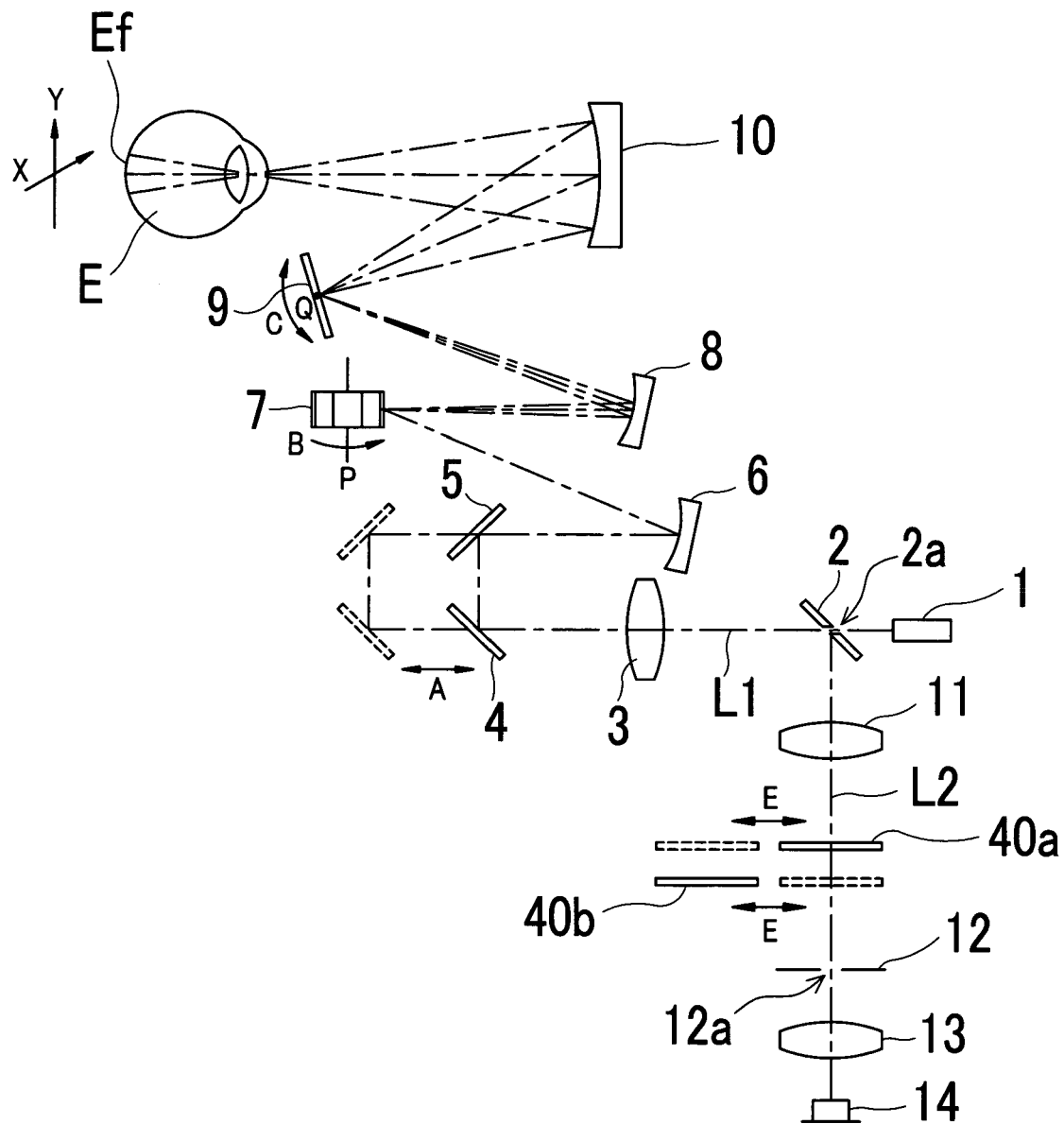
FIG. 7 is a view showing another example of a filter changing mechanism.
Figure 8:
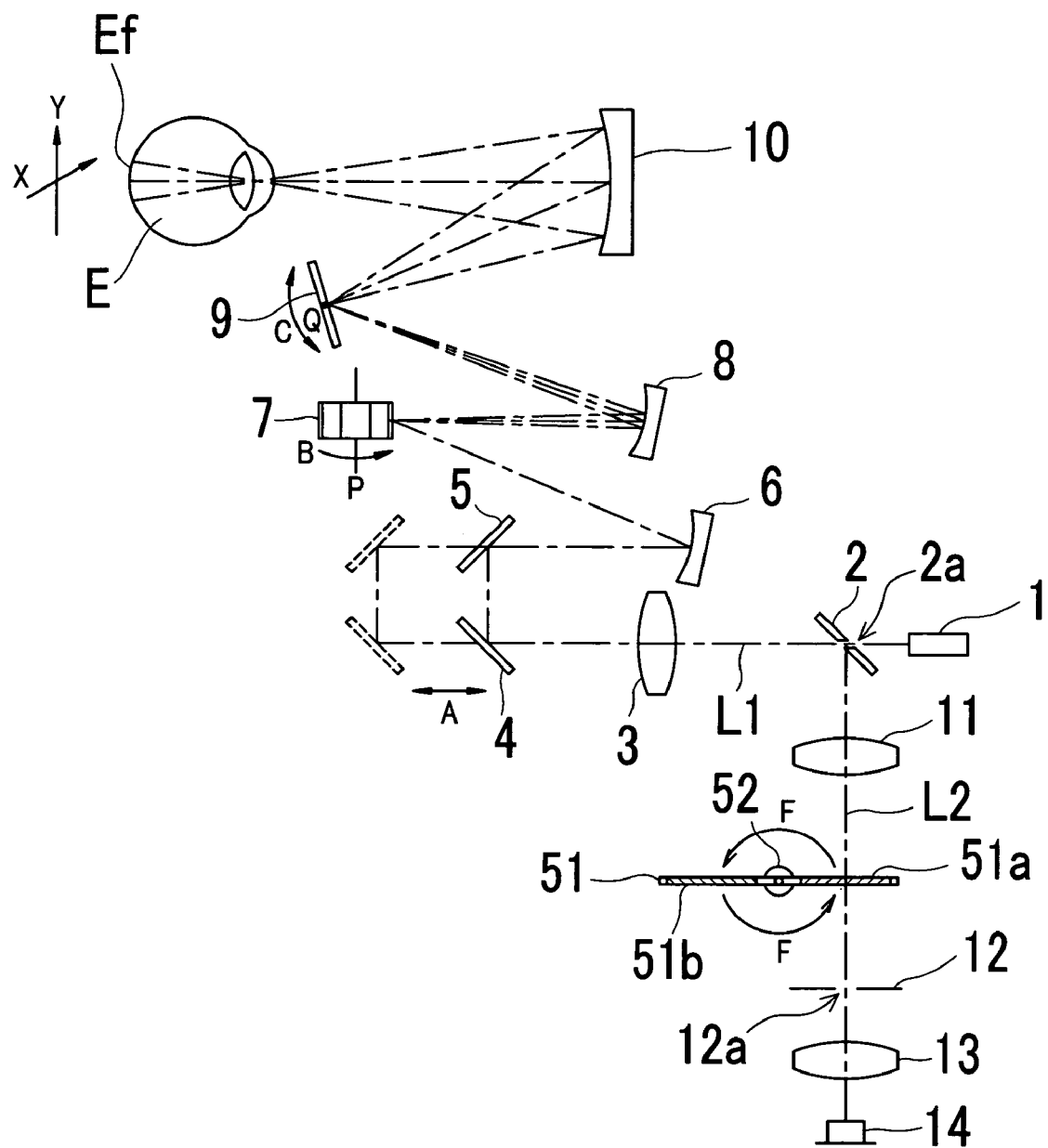
FIG. 8 is a view showing another example of a filter changing mechanism.

Although filter changing is performed by rotation of the filter disc 20 in the direction D as shown in FIG. 1, it may be arranged to alternately dispose at least two filters (two types of filters) in the optical path of the imaging optical system and obtain different types of moving images in sync with the changing. For instance, as shown in FIG. 7, two filters 40a and 40b may be inserted/withdrawn (moved) in a direction indicated by an arrow E to be alternately disposed in the optical system of the imaging optical system. As shown in FIG. 8, alternatively, a filter disc 50 on which two filters 51a and 51b are mounted in place may be rotated in a direction indicated by an arrow F by a rotator 52 such as a motor, thereby alternately disposing the filters 51a and 51b in the optical path of the imaging optical system.

The filter disc 20 may be provided with, instead of the openings 26, a filter that transmits only the infrared, first beam as illumination light for observation. In case of using the visible, second beam as illumination light for observation, a filter that transmits only the visible, second beam may be provided.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A fundus imaging apparatus comprising:
    a beam emitter which simultaneously emits a first laser beam and a second laser beam having a different wavelength from the first beam;
    an irradiation optical system having a beam scanner which scans the emitted first and second beams in two dimensions on a fundus, the irradiation optical system being adapted to irradiate the emitted first and second beams onto the fundus;
    a first filter which intercepts the first and second beams reflected by the fundus and second fluorescence from the fundus by irradiation of the second beam and transmits first fluorescence from the fundus by irradiation of the first beam;
    a second filter which intercepts the first and second beams reflected by the fundus and the first fluorescence from the fundus and transmits the second fluorescence from the fundus;
    an imaging optical system adapted to receive, by a single photo-receiving element, the first fluorescence having passed through the first filter and the second fluorescence having passed through the second filter;
    a filter changer which continuously alternately disposes the first filter and the second filter in an optical path of the imaging optical system in sync with scanning by the beam scanner; and
    an image processing part which alternatively obtains a received light signal of the first fluorescence and a received light sianal of the second fluorescence through the photo-receiving element to obtain a first fluorescent fundus image based on the received light signal of the first fluorescence from the photo-receiving element and obtains a second fluorescent fundus image based on the received light signal of the second fluorescence from the photo-receiving element.

2. The fundus imaging apparatus according to claim 1, wherein the filter changer includes a rotary disc on which the first and second filters are arranged and a rotator which rotates the rotary disc.

3. The fundus imaging apparatus according to claim 2, wherein the rotary disc is provided with an opening between the first and second filters.

4. The fundus imaging apparatus according to claim 1, wherein the beam scanner includes a polygon mirror which scans the first and second beams in a predetermined direction and a galvano mirror which scans the first and second beams in a direction perpendicular to the scanning direction of the polygon mirror, and
    the filter changer is adapted to continuously alternately dispose the first and second filters in sync with scanning of the galvano mirror.

5. A fundus imaging method comprising the steps of:
    simultaneously emitting a first laser beam and a second laser beam having a wavelength different from the first beam and scanning the emitted first and second beams in two dimensions on a fundus;
    continuously and alternately receiving, by a single photo-receiving element, first fluorescence from the fundus resulting from the first beam and second fluorescence from the fundus resulting from the second beam in sync with scanning of the first and second beams; and
    obtaining a first fluorescent fundus image based on a received light signal of the first fluorescence and a second fluorescent fundus image based on a received light signal of the second fluorescence in alternate manner every one frame.

* * * * *